United States Patent

Zambounis et al.

[11] Patent Number: 5,725,651
[45] Date of Patent: Mar. 10, 1998

[54] MONO-N-ALKYL-QUINACRIDONE PIGMENTS

[75] Inventors: John Zambounis, Basel, Switzerland; Jin Mizuguchi, Yokohama, Japan

[73] Assignee: Ciba Specialty Chemicals Corporation, Tarrytown, N.Y.

[21] Appl. No.: 793,933
[22] PCT Filed: Sep. 2, 1995
[86] PCT No.: PCT/EP95/03463
§ 371 Date: Mar. 10, 1997
§ 102(e) Date: Mar. 10, 1997
[87] PCT Pub. No.: WO96/08536
PCT Pub. Date: Mar. 21, 1996

[30] Foreign Application Priority Data

Sep. 14, 1994 [GB] United Kingdom ............ 9418495

[51] Int. Cl.$^6$ ................................ C09B 48/00
[52] U.S. Cl. ............ 106/497; 106/495; 252/301.16; 313/504; 428/690; 546/56; 546/57
[58] Field of Search ................ 106/495, 497; 546/56, 57; 252/301.16; 313/504; 428/690

[56] References Cited

U.S. PATENT DOCUMENTS 4,632,704  12/1986  Bäbler ........................ 106/498
4,760,004  7/1988  Rochat et al. ................ 430/58
5,227,252  7/1993  Murayama et al. ........... 428/390
5,593,788  1/1997  Shi et al. ..................... 428/690

FOREIGN PATENT DOCUMENTS 0190999  8/1986  European Pat. Off.
0267873  5/1988  European Pat. Off.

OTHER PUBLICATIONS

Chem. Abstract vol. 101, No. 26, Dec. 24, 1984, abstract No. 231927c, Pushkina et al.
Chem. Abstract vol. 95, No. 12, Sep. 21, 1981, abstract No. 105566, Shcherbo et al.
Chem. Abstract vol. 90, No. 24, Jun. 11, 1979, abstarct No. 195019 Shcherbo et al.
Derwent Japanese Patent Report abstr. nr. 22416/69 yosho naga (Sep. 25, 1969).
J. Phys. Chem. Ref. Data, vol. 16, No. 2, (1987) pp. 239–260 (No Month Avail.).
Chem. Rev., vol. 67, No. 1, Jan. 25, 1967, pp. 1–3.

Primary Examiner—Mark L. Bell
Assistant Examiner—Scott L. Hertzog
Attorney, Agent, or Firm—Kevin T. Mansfield

[57] ABSTRACT

Mono-N-alkyl-quinacridone pigments are disclosed. They exhibit high light fastness, high temperature stability and high migration fastness. Moreover, they show hypsochromic shifts, fluorescence and high photoconductivity. These pigments are suited for coloring high molecular weight organic materials, for use as light emitting materials of organic electroluminescent elements as well as photoreceptors of electrophotography.

17 Claims, No Drawings

MONO-N-ALKYL-QUINACRIDONE PIGMENTS

The instant invention relates to mono-N-alkyl-quinacridone pigments. Quinacridones are well known as valuable organic pigments, in particular as colouring materials for high molecular weight organic materials (see, for example, S.S. Labena et al. Chem. Rev., 67, 1 (1967).

On the other hand, Carmichael et al. J. Phys. Chem. Ref. Data, 16, 239 (1987) describes spectral properties of N-methyl-quinacridone in solution.

However, Carmichael et al neither disclose nor suggest the properties and the method of production of N-methyl-quinacridone pigment.

Accordingly, nothing is known about N-alkyl-quinacridone pigments, in particular that they exhibit the following surprising properties:

1) excellent pigment properties, such as lightfastness, temperature stability over 400° C. and migration fastness, enabling the application of these pigments as colouring materials for high molecular weight organic materials, such as natural or synthetic resins, e.g. polyolefins, polyesters and polyamides;

2) hypsochromic shifts, which cannot be obtained by conventional quinacridones;

3) fluorescence, which cannot be obtained by conventional quinacridones, taking place under irradiation with visible light (around 490 nm wavelength), enabling the application of the pigments as fluorescent pigments as well as light emitting materials of organic electroluminescent elements;

4) high photoconductivity, which cannot be obtained by conventional quinacridones, taking place under irradiation with light of 400–600 nm wavelength, enabling the application of the pigments as photoreceptors for electrophotography and solar cells.

The invention relates to:

a N-alkyl-quinacridone pigment possessing the above mentioned properties represented by formula

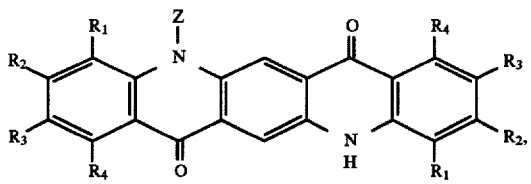

wherein Z is $C_1$–$C_{18}$-alkyl which is unsubstituted or substituted by F, Cl, Br, —OH, —O—$C_1$–$C_{18}$-alkyl, $C_3$–$C_7$-cycloalkyl, phenyl or naphthyl; $R_1$, $R_2$, $R_3$ and $R_4$ are each independently of the other (i) H, (ii) F, Cl or Br, (iii) —OH, (iv) —CN, (v) —$NO_2$, (vi) $C_1$–$C_{18}$-alkyl, phenyl or naphthyl, which alkyl, phenyl or naphthyl is unsubstituted or substituted by F, Cl, Br, —OH, —CN, —$NO_2$, pheny or naphthyl, which phenyl or naphthyl is unsubstituted or substituted by F, Cl, Br, $C_1$–$C_{18}$-alkyl or —O—$C_1$–$C_{18}$-alkyl, a heterocyclic aromatic residue, —$OCOR_5$, —$OR_6$, —$COOR_5$, —$N(R_6)(R_7)$ or —$CON(R_6)(R_7)$, in which $R_5$ is $C_1$–$C_{18}$-alkyl, phenyl, naphthyl or benzyl, which alkyl, phenyl, naphthyl or benzyl is unsubstituted or substituted by F, Cl, Br, $C_1$–$C_{18}$-alkyl or —O13 $C_1$–$C_{18}$-alkyl, and in which $R_6$ and $R_7$ are each independently of the other $C_1$–$C_{18}$-alkyl which is unsubstituted or substituted by —CN or —OH; $C_3$–$C_7$-cycloalkyl, phenyl or naphthyl, which cycloalkyl, phenyl or naphthyl is unsubstituted or substituted by F, Cl, Br, $C_1$–$C_{18}$-alkyl or —O—$C_1$–$C_{18}$-alkyl, or $R_6$ and $R_7$ together with the N atom form a 5-membered or 6-membered hetero ring; (vii) —$OR_8$, in which $R_8$ is $C_1$–$C_{18}$-alkyl, phenyl, naphthyl or $C_3$–$C_7$-cycloalkyl, which alkyl, phenyl, naphthyl or cycloalkyl is unsubstituted or substituted by F, Cl, Br, $C_1$–$C_{18}$-alkyl or —O—$C_1$–$C_{18}$-alkyl, or benzyl, (viii) —$SR_8$, (ix) —$N(R_6)(R_7)$, (x) —$COOR_5$, (xi) —$N(R_9)COR_5$, in which $R_9$ is $C_1$–$C_{18}$-alkyl, phenyl, naphthyl or $C_3$–$C_7$-cycloalkyl, which alkyl, phenyl, naphthyl or cycloalkyl is unsubstituted or substituted by F, Cl, Br, $C_1$–$C_{18}$-alkyl or —O—$C_1$–$C_{18}$-alkyl, benzyl or the residue —$COR_5$, or in which $R_9$ together with the N atom form a heterocyclic ring, (xii) —$N(R_8)COOR_5$, (xiii) —$NR_8CON(R_6)(R_7)$, (xiv) —$SO_2R_5$ or —$SOR_5$, (xv) —$SO_2OR_5$, (xvi) —$CON(R_6)(R_7)$, (xvii) —$SO_2N(R_6)(R_7)$, (xviii) —N=N-$R_{10}$, in which $R_{10}$ is the residue of a coupling component, or phenyl which is unsubstituted or substituted by F, Cl, Br, $C_1$–$C_{18}$-alkyl or —O—$C_1$–$C_{18}$-alkyl, benzyl or the residue —$COR_5$, or (xix) —$OCOR_5$, in which substituents (ix)–(xiv) $R_5$, $R_6$ and $R_7$ are as defined under (vi) and $R_8$ is as defined under (vii), except the compound in which $R_1$, $R_2$, $R_3$ and $R_4$ are H and Z is methyl, a process for producing the pigments of formula I and/or the pigment represented by formula

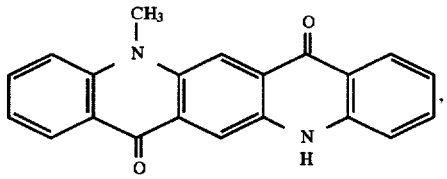

the application of the pigments of formula I and/or the pigment represented by formula

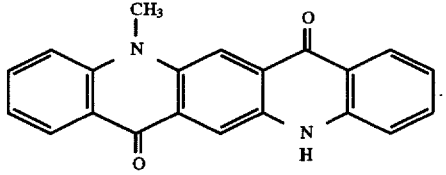

In the above definition, the alkyl can be straight-chain or branched. Examples of the alkyl are methyl, ethyl and the isomers of propyl, butyl, pentyl, hexyl, heptyl, octyl nonyl, decyl, undecyl, dodecyl, tetradecyl, hexadecyl and octadecyl. The alkyl is preferably $C_1$–$C_{12}$ alkyl, more preferably $C_1$–$C_8$ alkyl, and most preferably $C_1$–$C_4$ alkyl. Examples of such most preferred alkyl is methyl, ethyl, n- and i-propyl, n-, i- and t-butyl.

The cycloalkyl is preferably $C_5$–$C_7$-cycloalkyl, especially cyclopentyl and cyclohexyl.

Heterocyclic aromatic residues as substituents for the alkyl, phenyl or naphthyl as $R_1$, $R_2$, $R_3$ or $R_4$ are, for example, 2-thienyl, 2-benzoxazolyl, 2-benzothiazolyl, 2-benzimidazolyl, 6-benzimidazolonyl, 2-, 3- or 4-pyridyl or 2-, 4- or 6-quinolyl residues.

The 5- or 6-membered hetero rings which $R_6$ and $R_7$ together with the N atom can form are for example morpholine, piperidine or phthalimide rings.

Examples of unsubstituted or substituted alkyl, phenyl or naphthyl groups as $R_1$, $R_2$, $R_3$ or $R_4$ are methyl, ethyl, n- or i-propyl, n-, i- or t-butyl, t-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluomethyl, cyanomethyl, methoxycarbonylmethyl, acetoxymethyl, benzyl, phenyl, o-, m- or p-methylphenyl, o-, m- or p-chlorophenyl, and naphthyl.

In —$OR_8$ as $R_1$, $R_2$, $R_3$ or $R_4$, $R_8$ is for example methyl, ethyl, n- or i-propyl, trifluoroethyl, phenyl, o-, m- or p-chlorophenyl, o-, m- or p-methylphenyl, α- or β-naphthyl, cyclohexyl or benzyl.

In —$SR_8$ as $R_1$, $R_2$, $R_3$ or $R_4$, $R_8$ is for example methyl, ethyl, n- or i-propyl, phenyl, o-, m- or p-chlorophenyl, o-, m- or p-ethylphenyl, α- or β-naphthyl, cyclohexyl or benzyl.

Examples of —$N(R_6)(R_7)$ as $R_1$, $R_2$, $R_3$ or $R_4$ include dimethylamino, diethylamino, N,N-bis-(β-hydroxyethyl)-amino, N,N-bis-(β-cyanoethyl)-amino, N-methylphenylamino and dibenzylamino.

In —$COOR_5$ as $R_1$, $R_2$, $R_3$ or $R_4$, $R_5$ is for example methyl, ethyl, n- or i-propyl, n-, i- or t-butyl, phenyl or benzyl.

Examples of —$N(R_9)COR_5$ as $R_1$, $R_2$, $R_3$ or $R_4$ are N-methylacetylamino, N-methylpropyonylamino, N-ethylbutyrylamino, N-methylbenzoylamino, N-succinimido and N-phthalimido.

Examples of —$N(R_8)COOR_5$ as $R_1$, $R_2$, $R_3$ or $R_4$ include —$N(CH_3)COOCH_3$, —$N(CH_3)COOC_2H_5$ and —$N(C_2H_5)COOC_6H_5$.

Examples of —$N(R_8)CON(R_6)(R_7)$ as $R_1$, $R_2$, $R_3$ or $R_4$ include —$N(CH_3)CON(CH_3)_2$, —$N(CH_3)CON(C_2H_5)_2$, —$N(CH_3)CON(CH_3)(C_6H_5)$ and —$N(C_6H_5)CON(CH_3)_2$.

Examples of —$SO_2R_5$ or —$SOR_5$ as $R_1$, $R_2$, $R_3$ or $R_4$ are methylsulfonyl, ethylsulfonyl, phenylsulfonyl, 2-naphthylsulfonyl and phenylsulfoxidyl.

In —$SO_2OR_5$ as $R_1$, $R_2$, $R_3$ or $R_4$, $R_5$ is for example methyl, ethyl, phenyl, o-, m- or p-chlorophenyl, o-, m- or p-methylphenyl, α- or β-naphthyl.

Examples of —$CON(R_6)(R_7)$ as $R_1$, $R_2$, $R_3$ or $R_4$ include N,N-dimethylcarbamoyl, N-methyl-N-ethylcarbamoyl, N-methyl-N-phenylcarbamoyl, N-ethyl-N-α-naphthylcarbamoyl and N-piperidylcarbamoyl.

Examples of —$SO_2N(R_6)(R_7)$ as $R_1$, $R_2$, $R_3$ or $R_4$ are N,N-dimethylsulfamoyl, N-methyl-N-ethylsulfamoyl, N-methyl-N-phenylsulfamoyl and N-morpholylsulfamoyl.

In —N=N—$R_{10}$ as $R_1$, $R_2$, $R_3$ or $R_4$, $R_{10}$ is for example pyrazolyl, pyridonyl, o-, m- or p-hydroxyphenyl, o-hydroxynaphthyl or p-N,N-dimethylaminophenyl.

In —$OCOR_5$ as $R_1$, $R_2$, $R_3$ or $R_4$, $R_5$ is for example methyl, ethyl, phenyl, o-, m- or p-chlorophenyl.

Preferred pigments are those of formula (I) wherein Z is $C_1$–$C_{12}$-alkyl, and $R_1$, $R_2$, $R_3$ and $R_4$ are each independently of the other H, F, Cl, —CN, trifluoromethyl, $C_1$–$C_{12}$-alkyl, $C_1$–$C_{12}$-alkoxy, $C_1$–$C_{12}$-alkylmercapto, $C_2$–$C_{12}$-alkoxycarbonyl, $C_2$–$C_{24}$-dialkylamino, phenyl, phenoxy, phenylmercapto or phenoxycarbonyl, except that in which $R_1$, $R_2$, $R_3$ and $R_4$ is H and Z is methyl.

More preferred pigments are those of formula (I) wherein Z is $C_1$–$C_8$-alkyl, and $R_1$, $R_2$, $R_3$ and $R_4$ are each independently of the other H, F, Cl, —CN, trifluoromethyl, $C_1$–$C_8$-alkyl, $C_1$–$C_8$-alkoxy, $C_1$–$C_8$-alkylmercapto, $C_2$–$C_{16}$-dialkylamino or phenyl, except that in which $R_1$, $R_2$, $R_3$ and $R_4$ are H and Z is methyl.

Most preferred pigments are those of formula (I) wherein Z is $C_1$–$C_4$-alkyl, $R_1$, $R_2$ and $R_4$ is H, and $R_3$ is H, Cl or $C_1$–$C_4$-alkyl, except that in which $R_1$, $R_2$, $R_3$ and $R_4$ are H and Z is methyl.

The N-alkyl-quinacridone pigment of formula (I) or the pigment represented by formula

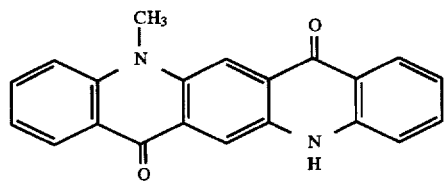

can be produced, for example, by subjecting a quinacridone represented by formula II

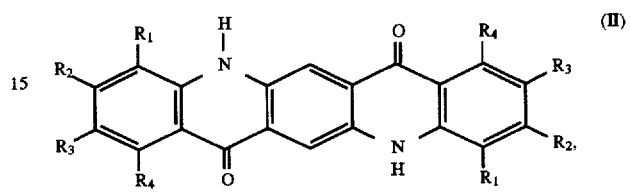

wherein $R_1$, $R_2$, $R_3$ and $R_4$ have the hereinbefore given meaning, to a N-deprotonation reaction in an organic solvent using a base, and then alkylating said quinacridone using an alkylating agent.

The compounds represented by formula (II) are known compounds. If some of them are new, they can be produced in analogy to generally known methods.

As solvents to be used in the above process, polar organic solvents are preferred. Examples of such solvents are ethers, such as tetrahydrofuran or dioxane, or glycol ethers, such as ethylene glycolmethyl ether, ethylene glycolethyl ether, acetonitrile, benzonitrile, N,N-dimethylformamide, N,N-dimethylacetamide, nitrobenzene, N-methylpyrrolidone, halogenated aliphatic or aromatic hydrocarbons such as trichloroethane, benzene or benzene substituted by alkyl, alkoxy or halogen, e.g., toluene, xylene, anisole or chlorobenzene, or aromatic N-heterocycles, such as pyridine, picoline or quinoline. These solvents can be used also as mixtures.

Especially preferred solvents are, for example, tetrahydrofuran, N,N-dimethylformamide, dioxane, dimethylsulfoxide, N,N-dimethylacetamide or N-methylpyrrolidone.

The bases eligible for use in the N-deprotonation step of the instant process are, for example, the alkali metals themselves, such as lithium, sodium or potassium as well as their hydroxides and carbonates, or alkali metal amides, such as lithium, sodium or potassium amide or alkali metal hydrides, such as lithium, sodium or potassium hydride, or alkaline earth or alkaline metal alcoholates, which are derived especially from primary, secondary or tertiary aliphatic alcohols with 1 to 10 C-atoms, e.g., lithium, sodium or potassium methylate, ethylate, n-propylate, isopropylate, n-butylate, sec.-butylate, tert.-butylate, 2-methyl-2-butylate, 2-methyl-2-pentylate, 3-methyl-3-pentylate, 3-ethyl-3-pentylate, and further, preferably, organic aliphatic, aromatic or heterocyclic N-bases, especially, for example, diazabicyclooctene, diazabicycloundecene, trialkylamines, such as trimethyl- or triethylamine, pyridine and substituted pyridines, such as 4-dimethylaminopyridine. The above bases can be used also as mixtures.

Especially preferred bases are inorganic bases, for example, alkali metals themselves, e.g. lithium, sodium and potassium, their hydroxides and carbonates, and, in particular, anhydrous alkali metal hydrides, e.g. lithium hydride, sodium hydride and potassium hydride.

The N-deprotonation reaction is accomplished simply by adding the compound of formula (II) and the base to the organic solvent, and then stirring the thus prepared suspension.

The compound of formula (II) and the base are added in a molar ratio of 1:0.01–100, preferably 1:0.1–10, more preferably 1:0.5–5, and most preferably 1:0.5–2.

The above components are added to the organic solvent such that the concentration of the compound of formula (II) is 0.0001–10 mol/l, preferably 0.001–1 mol/l, more preferably 0.01–0.5 mol/l, and most preferably 0.02–0.1 mol/l.

The deprotonation reaction is accomplished at a temperature of −10° C. to 100° C., preferably 0° C. to 50° C., and most preferably 10° C. to 40° C.

The reaction is accomplished in 1–72 hours, preferably 1–48 hours, and most preferably 1–24 hours.

Preferably, the reaction is carried out in an inert atmosphere such as $N_2$, He or Ar atmosphere.

If the suspension after the N-deprotonation step contains solid content, it is advantageous to remove said solid component by filtration, preferably in an inert atmosphere as exemplified above.

The alkylation step is carried out by reacting the N-deprotonated intermediate with an appropriate methylating agent. This is done by simply adding said alkylating agent to the above reaction mixture or the filtrate containing the N-deprotonated intermediate.

Examples of alkylating agents eligible for use for the alkylating step are halide of formula

ZX     (III), sulfonic acid esters of formula

A—SO$_2$—OZ     (IV), dialkyl carbonates of formula

Z—O—CO—O—Z     (V), dialkyl sulfates of formula

Z—O—SO$_2$—O—Z     (VI), oxonium salts of formula $(B_3O)^{\oplus}U^{\ominus}$     (VII), alkyl perchlorates of formula ZClO$_4$     (VIII)

or alkyl halogensulfonates of formula

X—SO$_2$—OZ     (IX), wherein Z has the hereinbefore given meaning, X is F, Cl, Br or I, A is H, $C_1$–$C_4$-alkyl or phenyl, which alkyl or phenyl is unsubstituted or substituted by F, Cl, Br or $C_1$—$C_4$-alkyl, B is H, Z, $C_5$–$C_7$-cycloalkyl or phenyl, which cycloalkyl or phenyl is unsubstituted or substituted by F, Cl, Br or $C_1$–$C_4$-alkyl, with the proviso that at least one of B is Z, and Y is $F^{\ominus}$, $Cl^{\ominus}$, $Br^{\ominus}$, $I^{\ominus}$, $BF_4^{63}$, $PF_6^{63}$, $AsF_6^{63}$, $SbF_6^{\ominus}$, $FSO_3^{\ominus}$ or the anion of an organic sulfonic acid or carboxylic acid.

The compounds (II)–(IX) are known compounds. If some of them are new, they can be produced in analogy to generally known methods.

Preferred alkylating agents are alkyl halides of formula III, especially alkyl iodides, and dialkyl sulfates of formula VI.

The above alkylating agents are used in an amount of 0.01–100, preferably 0.1–10, more preferably 0.5–5, and most preferably 0.5–2 mol per 1 mol of the compound of formula II.

This step is carried out preferably in an inert atmosphere as exemplified hereinbefore. The reaction temperature is preferably 0°–50° C., especially 10°–40° C. The alkylation usually completes rapidly.

Since the product, obtained as a precipitate, is in general a mixture of N-alkyl-quinacridone and N,N'-dialkyl-quinacridone, it is generally necessary to separate the former from the latter if a pure N-alkyl-quinacridone is desired.

The separation can be achieved, for example, by reacting the mixture composed of N-alkyl-quinacridone and N,N'-dialkyl-quinacridone with a base in an organic solvent, removing the solid content left thereafter by filtration, and then reacting the filtrate with an acid.

Prior to this separation process, it is preferred that the mixture composed of N-alkyl-quinacridone and N,N'-dialkyl-quinacridone is separated from the reaction mixture by filtration, washed with solvents such as those as mentioned above or water, and dried. The drying can be accomplished in air.

As organic solvents eligible for use in the separation step, those mentioned hereinbefore including the preferred ones can be advantageously used.

The bases to be used for this step are the same as those mentioned hereinbefore including the preferred ones.

The reaction between the mixture composed of N-alkyl-quinacridone and N,N'-dialkyl-quinacridone with the base is carried out simply by suspending the mixture in the organic solvent, then adding the base thereto and stirring the reaction system.

The reaction conditions for this step are the same as those for the N-deprotonation reaction as mentioned hereinbefore, including the preferred ones. After the completion of this reaction, the N-alkyl-quinacridone is present in the reaction system as dissolved anions whilst the N,N'-dialkyl-quinacridone is present as solvent-insoluble crystals.

The filtration is carried out preferably in an inert atmosphere as exemplified hereinbefore. In this filtration step, the N,N'-dialkyl-quinacridone is removed from the reaction system.

Acids eligible for use for the reaction with the filtrate obtained in the above step, are inorganic acids, organic acids and water.

Examples of inorganic acids include HF, HCl, HBr, HI, HCN, $HNO_3$, $HNO_2$, $H_2SO_4$, $H_2SO_3$, $H_2CO_3$, $H_3PO_4$, $HClO_4$ and $NH_4Cl$.

Examples of organic acids include aliphatic sulfonic acids, such as methanesulfonic acid, aliphatic carboxylic acids, such as formic acid, acetic acid and propionic acid, substituted aliphatic carboxylic acids, such as trifluoroacetic acid, aliphatic dicarboxylic acids, such as oxalic acid, malonic acid and citric acid, cycloaliphatic sulfonic or carboxylic acid, such as cyclohexanecarboxylic acid and campher-10-sulfonic acid, aromatic sulfonic acids, such as benzenesulfonic acid, toluenesulfonic acid and ethylbenzenesulfonic acid, heterocyclic aromatic sulfonic acids, such as pyridinesulfonic acid, aromatic carboxylic acids, such as benzoic acid, aromatic dicarboxylic acids, such as phthalic acid, heterocyclic aromatic carboxylic acids, such as pyridinecarboxylic acid, and araliphatic carboxylic acids, such as benzylcarboxylic acid and cinnamic acid.

Any acid including water can be used for the reaction with the filtrate.

The reaction between the acid and the filtrate is accomplished by simply adding the acid to the filtrate.

The acid is used in an amount of 0.01–100, preferably 0.1–10, more preferably 0.5–5, and most preferably 0.5–2 mol per 1 mol of the compound of formula II.

This reaction is carried out at a temperature of −10° C.–100° C., preferably 0° C.–50° C., most preferably 10°–40° C., preferably in an inert atmosphere as exemplified hereinbefore.

The reaction is usually complete within 1 hour.

After the completion of this reaction, the N-alkyl-quinacridone is obtained as a precipitate in very high purity.

The product thus separated is then washed with solvents as mentioned hereinbefore including the preferred ones or water, and subsequently dried in air, thereby yielding the N-alkyl-quinacridone pigment of the instant invention.

The pigments represented by formula I and the pigment represented by formula

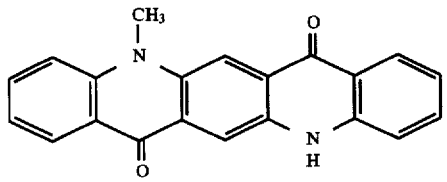

exhibit the following surprising properties:

1) excellent pigment properties, such as lightfastness, temperature stability over 400° C. and migration fastness;

2) hypsochromic shifts, which cannot be obtained by conventional quinacridones;

3) fluorescence, which cannot be obtained by conventional quinacridones, taking place under irradiation with visible light (around 490 nm wavelength);

4) high photoconductivity, which cannot be obtained by conventional quinacridones, taking place under irradiation with light of 400–600 nm wavelength.

Because of these excellent properties, the pigments represented by formula I and the pigment of formula

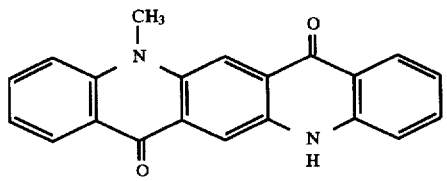

can be advantageously used as colouring agents (polymer-soluble dyes, or pigments in the conventional sense) for colouring high molecular weight organic materials in new shade, due to their hypsochromic shifts and fluorescence, as light-emitting materials of organic electroluminescent elements, due to the above mentioned fluorescent property, or as photoconductors of electrophotographic photoreceptors or solar cells, due to their high photoconductivity.

When the pigments of formula I or the pigment represented by formula

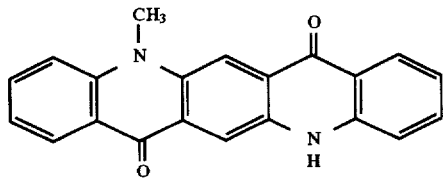

are used as polymer-soluble dyes, the polymers to be dyed are, for example, polystyrene, polyamides, ABS and, in particular, linear polyesters. Examples of linear polyesters are in particular those which are obtained by polycondensation of terephthalic acid or ethers thereof with glycols of the formula HO—(CH$_2$)$_n$—OH, in which n is a number from 2 to 10, or with 1,4-di-(hydroxymethyl)-cyclohexane, or by polycondensation of glycol ethers of hydroxybenzoic acids, for example p-(β-hydroxyethoxy)-benzoic acid. The term linear polyesters also includes copolyesters which are obtained by replacing some of the terephthalic acid by another dicarboxylic acid and/or replacing some of the glycol by another diol.

However, the polyethylene terephthalates are of particular interest.

The linear polyesters to be dyed are advantageously mixed intimately with the pigment in the form of powder, chips or granules. This mixing can be effected, for example, by coating the polyester particles with the finely divided dry powder or by treating the polyester particles with a solution or dispersion of the pigment in an organic solvent and then removing the solvent.

The material to be dyed can also be dyed by the bath-dyeing method.

Mixtures of the pigments of the invention and mixtures of one or more pigments of the invention with disperse dyes can be used to adjust the shade.

Finally, the pigment can also be added directly to the molten polyester or before or during polycondensation of the polyethylene terephthalate.

The ratio of pigment to polyester can vary within wide limits, depending on the desired depth of shade. In general, it is advisable to use 0.01–3 parts of pigment per 100 parts of polyester.

The polyester particles thus treated are melted in an extruder by known processes and are pressed to articles, in particular films or fibers, or cast to sheets.

When the pigments of the invention are used as pigments in the conventional sense for high molecular weight organic materials, it is advantageous to convert the pigments nto a finely disperse form. This can be effected in various ways, for example:

(a) by grinding or kneading, advantageously in the presence of grinding assistants, such as inorganic or organic salts, with or without the addition of organic solvents. After the grinding, the assistants are removed in the customary manner, for example soluble inorganic salts or removed with water and water-insoluble organic solvents are removed by, for example, steam distillation;

(b) by reprecipitation from sulfuric acid, methanesulfonic acid, trichloroacetic acid or polyphosphoric acid.

It may prove advantageous to after-treat the pigments treated according to (a) or (b) with organic solvents, preferably with those which have boiling points above 100° C.

Solvents which prove to be particularly suitable are benzenes which are substituted by halogen atoms or alkyl or nitro groups, such as the xylenes, chlorobenzene, o-dichlorobenzene or nitrobenzene, and pyridine bases, such as pyridine, picoline or quinoline, and furthermore ketones, such as cyclohexanone, ethers, such as ethylene glycol monomethyl or monoethyl ether, amides, such as dimethylformamide or N-methyl-pyrrolidone, and dimethyl sulfoxide, sulfolane or water by itself, if necessary under pressure. The aftertreatment can also be carried out in water in the presence of organic solvents and/or with the addition of surface-active substances, or aliphatic amines or with liquid ammonia.

Depending on the intended use, it proves to be advantageous to use the pigments as toners or in the form of preparations.

The high molecular weight organic material can be of natural or synthetic origin. It can be, for example, a natural resin or a drying oil, rubber or casein or a modified natural substance such as chlorinated rubber, oil-modified alkyd resins or viscose, a cellulose ether or ester such as cellulose acetate, cellulose propionate, cellulose acetobutyrate or nitrocellulose, or, in particular, a man-made synthetic organic polymer (thermoset or thermoplastic), such as those obtained by polymerisation, polycondensation or polyaddition. Polymerisation resins are, in particular, polyolefins, such as polyethylene, polypropylene or polyisobutylene, and furthermore substituted polyolefins, such as polymers of vinyl chloride, vinyl acetates, styrene, acrylonitrile, acrylates and/or methacrylates or butadiene, and copolymers of the monomers mentioned, in particular ABS or EVA.

Polyaddition and polycondensation resins are the condensation products of formaldehyde with phenols, the so-called phenoplasts, and the condensation products of formaldehyde with urea, thiourea and melamine, the so-called aminoplasts, the polyesters used as surface-coating resins, and in particular both those which are saturated, for example alkyd resins, and those which are unsaturated, for example maleate resins, and furthermore linear polyesters and polyamides or silicones.

The high molecular weight compounds mentioned can be used by themselves or in mixtures, as plastic compositions or melts, which may, if appropriate, be spun to fibers.

They can also be in the form of their monomers or in the polymerised state in dissolved form as film-forming agents or binders for varnishes or printing inks, for example linseed oil varnish, nitrocellulose, alkyd resins, melamine resins and urea/formaldehyde resins or acrylic resins.

The high molecular weight organic substances are pigmented with the pigments of the invention, for example, by mixing such a pigment, if appropriate in the form of a masterbatch, with these substrates using roll mills or mixing or grinding apparatus. The pigmented material is then brought into the desired final form by processes which are known per se, such as calendering, pressing, extrusion, brushing, casting or injection-moulding. It is frequently desirable to incorporate so-called plasticisers into the high molecular weight compounds before shaping in order to produce non-rigid shaped articles or to reduce their brittleness. Examples of suitable plasticisers are esters of phosphoric acid, phthalic acid or sebacic acid. In the process according to the invention, the plasticizers can be incorporated into the polymers before or after incorporation of the pigment. It is furthermore possible also to add fillers or other colouring constituents, such as white, coloured or black pigments, in any amounts, besides the pigments of the instant invention, to the high molecular weight organic substances for the purpose of achieving various colour shades.

For pigmenting varnishes and printing inks, the high molecular weight organic materials and the pigments of the invention are finely dispersed or dissolved in a common organic solvent or silvent mixture, if necessary together with additives, such as fillers, other pigments, siccatives or plasticisers. A procedure may be followed here in which the individual components are dispersed or dissolved by themselves, or several of them are dispersed or dissolved together, and only then are all the components brought together.

The resulting colorations, for example in plastics, fibres, varnishes or prints, are distinguished by an orange to red colour shade, a very good depth of shade, high saturation, good dispersibility, good fastness to overlacquering, migration, heat, light and weathering and a high gloss.

If the pigments of formula I or the pigment represented by formula

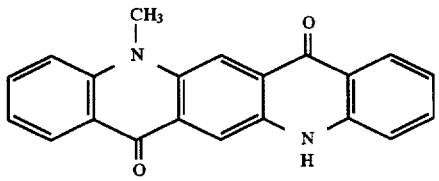

are to be used as fluorescent pigments, as light emitting materials of electroluminescent elements or as photoconductors of electrophotographic photoreceptors or of sollar cells, it is preferred that they be further purified prior to use. Such purification can be achieved advantageously by the sublimation method. Details of the sublimation technique is described, for example, in J. Mizuguchi, Krist. Tech., 16, 695-700 (1981). In this method, it is esential that a high temperature slightly lower than the sublimation point of the pigment of the invention remains constant over a long condensation region.

Electroluminescent elements using the pigment of formula I or the pigment represented by formula

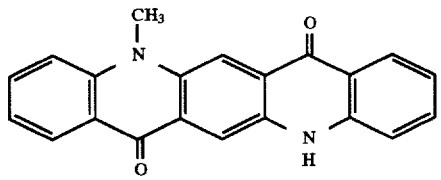

can be produed, for example, in the following manner: A hole transporting layer of 100-2000 Å thickness is formed on an ITO (indium-tin-oxide) glass by, for example, vacuum depositing a known organic hole transporting compound, such as polyvinyl carbazole, or by spin coating a solution containing such an organic compound and a binder, such as polycarbonate. Then, a light emitting layer having a thickness of 100-2000 Å comprising the pigment of the invention is formed on said hole transporting layer by, for example, vacuum depositing the pigment, or by spin coating a solution containing the pigment and a binder as above. Finally, an electrode is made on the light emitting layer by vacuum depositing a metal with a low ionisation potential, such as magnesium or indium or an alloy thereof. Electroluminescence with the emission maximum around 610 nm wavelength is obtained by flowing a direct current across the electroluminescent element with the ITO being the anode and the metal electrode being cathode.

The electrophotographic photoreceptor consists of a charge generating layer (photoconductor layer) and a charge transporting layer (a solid solution of e.g. hydrozones and polymers). Both layers are formed on a metalic substrate. The photoreceptor is integrally charged up, positively or negatively, by corona-discharging in order to form latent images. Then, the surface charge is neutralized by photo-irradiation in accordance with a master to be photocopied, which leads to the formation of a latent image. The thus obtained latent image is subsequently developed (visualized) using toner, and transferred onto a sheet of paper, followed by thermal fixation.

The electrophotographic photoreceptor using the pigment of formula I or the pigment represented by formula

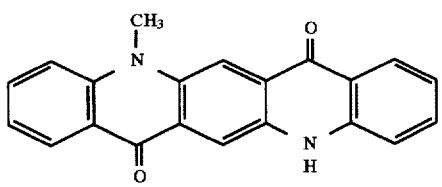

can be produced, for example, in the following manner: A photoconducting layer having a thickness of 1000–2000 Å comprising the pigment of the invention is formed on a metal substrate by, for example, vacuum depositing the pigment or by spin coating a solution containing the pigment and a binder such as a polycarbonate. Then, a hole transporting layer having a thickness of 5–20 μm is formed on the above photoconducting layer by, for example, spin coating or dip coating a solution containing a known hole transporting compound such as 4-dimethylaminobenzaldehyde-1,1-diphenylhydrazone and a binder as mentioned above. The thus produced photoreceptor shows charge acceptance of −800 V, and photosensitivity of 10 Lux.sec.

Solar cells using the pigment of formula I or the pigment represented by formula

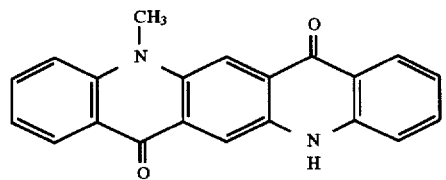

can be produced by, for example, vacuum depositing the pigment on an ITO glass, followed by the formation of an electrode on the pigment layer using a metal with a low ionisation potential, such as magnesium or indium, or an alloy thereof. The electrode is preferably formed by vacuum deposition method. When the thus made sollar cell is exposed to sun light, charge separation occurs across the interface between the pigment layer and ITO or between the pigment layer and the metal electrode, thereby generating a photoelectromotive force.

EXAMPLES

Example 1

(Synthesis of N-methylquinacridone)

1.54 g of sodium hydride is added to a suspension of 10 g (32 mmol) of quinacridone in 800 ml of dimethyl acetamide, and the mixture is stirred overnight in an inert atmosphere. The resulting dark blue solution, which also contains solid red portion, is filtered in an inert atmosphere, and the filtrate is reacted with 9 ml of methyl iodide. The orange coloured precipitate thereby formed is filtered, washed with dimethylacetamide and water and subsequently dried in air. The thus obtained substance (7.2 g in weight), which is a mixture composed of N,N'-dimethyl-quinacridone and mono-N-methyl-quinacridone, is suspended in 600 ml of dimethylacetamide and reacted with 1.54 g of sodium hydride, which suspension is stirred overnight in an inert atmosphere. The dark blue mixture formed is filtered in an inert atmosphere in order to isolate the insoluble orange coloured crystals of N,N'-dimethyl-quinacridone. The filtrate is reacted with 200 ml of a 0.2 N. aqueous hydrochloric acid solution. The red precipitate thereby formed is washed with dimethylacetamide, water and acetone, and subsequently dried in air. The yield (3.2 g) of pure N-methyl-quinacridone (red powder, indicated by formula A below) is 31%. The purity of the pigment is examined by means of elemental analysis and mass-spectrometry. The absorption maximum of an 800 Å thick vacuum deposited layer is observed around 540 nm, whilst that of quinacridone with the same thickness is around 560 nm.

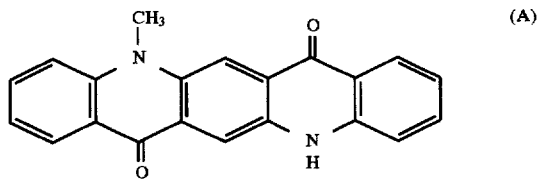

Example 2

(Synthesis of N-methyl-2,9-dimethyl-quinacridone)

0.071 g of sodium hydride is added to a suspension of 0.5 g (1.47 mmol) of 2,9-dimethylquinacridone in 30 ml of dimethylacetamide, and the mixture is stirred overnight in an inert atmosphere. The resulting dark blue mixture is filtered in an inert atmosphere, and the filtrate is reacted with 0.417 g of methyl iodide. The rose-red precipitate thereby formed is filtered, washed with dimethylacetamide and water and subsequently dried in air. This substance (0.17 g in weight) is suspended in 20 ml of dimethyl acetamide, 0.73 g sodium hydride is added thereto, and the suspension is stirred overnight. The dark blue mixture formed is filtered in an inert atmosphere, and the filtrate is acidified with a 0.2 N aqueous hydrochloric acid solution. The red precipitate thereby formed is washed with dimethyl acetamide, water and acetone, and subsequently dried in air. The yield (0.04 g) of pure N-methyl-2,9-dimethyl-quinacridone (rose powder, indicated by formula B below) is 8%. The purity of the pigment is examined by means of elemental analysis and mass-spectrometry.

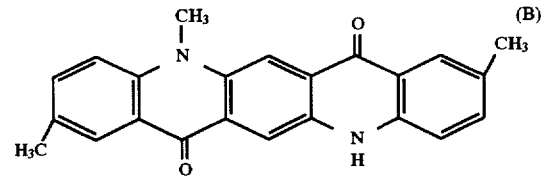

Example 3

(Synthesis of N-methyl-2,9-dichloro-quinacridone)

0.063 g of sodium hydride is added to a suspension of 0.5 g (1.3 mmol) of 2,9-dichloroquinacridone in 30 ml of dimethyl acetamide, and the mixture is stirred overnight in an inert atmosphere. The resulting dark blue mixture is filtered in an inert atmosphere, and the filtrate is reacted with 0.4 g of methyl iodide. The orange-red precipitate thereby formed is filtered, washed with dimethyl acetamide and water, and subsequently dried in air. This substance (0. 1 g in weight is suspended in 20 ml of dimethyl acetamide, 0.063 g of sodium hydride is added thereto, and the suspension is stirred overnight. The dark blue mixture formed is filtered in an inert atmosphere, and the filtrate is acidified with a 0.2 N aqueous hydrochloric acid solution. The red precipitate thereby formed is washed with dimethylacetamide, water and acetone, and subsequently dried in air. The yield (0.05 g) of pure N-methyl-2,9-dichloro-quinacridone (bordeaux-brown powder, indicated by formula C below) is 10%. The purity of the pigment is examined by means of elemental analysis and mass-spectrometry.

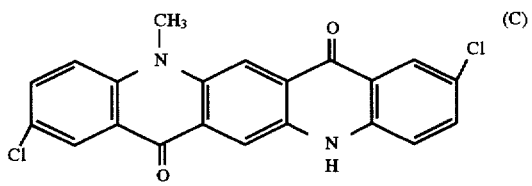

(C)

Properties of the above prepared N-methylquinacridones

1) Decomposition temperatures of the N-methylquinacridones are higher than 400° C.

2) PVC foils loaded with 0.2% N-methyl-quinacridone, N-methyl-2,9-dimethyl-quinacridone or N-methyl-2,9-dichloro-quinacridone each showed very high light stability.

3) The N-methylquinacridones exhibit excellent migration fastness in PVC.

Example 4

(Electrophotographic photoreceptor)

The pigment represented by formula

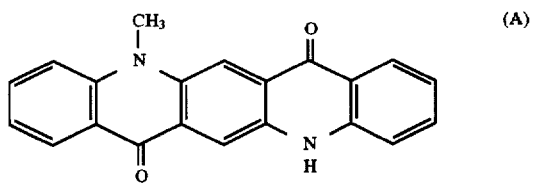

(A)

is vacuum deposited on an aluminum substrate as a charge generating material to a thickness of about 1500 Å under high vacuum. A solid solution consisting of polycarbonate and 4-diethylaminobenzaldehyde- 1,1-diphenylhydrozone (1:1 in weight ratio) is applied over the above charge generating layer using a spiral roll to a thickness of 15 µm. Subsequently, the charge transporting layer is dried at 60° C. for one hour. The electrophotographic chracteristics of this photoreceptor are evaluated using a "Paper Analyser" of Kawaguchi Denki (Modell SP-428). The charge acceptance is −800 V, and the photosensitivity $E_{1/2}$ in visible region is observed to be 10 Lux. Sec. ($E_{1/2}$ means the reciprocal value of the energy required for reducing the surface potential to half the initial value.)

What is claimed is:

1. A N-alkyl-quinacridone pigment represented by formula

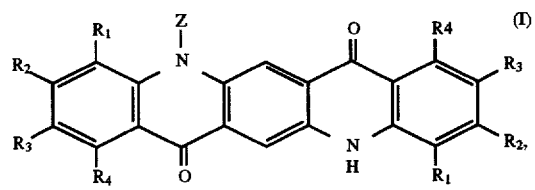

(I)

wherein Z is $C_1$–$C_{18}$-alkyl which is unsubstituted or substituted by F, Cl, Br, —OH, —O—$C_1$–$C_{18}$-alkyl, $C_3$–$C_7$-cycloalkyl, phenyl or naphthyl; $R_1$, $R_2$, $R_3$ and $R_4$ are each independently of the other (i) H, (ii) F, Cl or Br, (iii) —OH, (iv) —CN, (v) —NO$_2$, (vi) $C_1$–$C_{18}$-alkyl, phenyl or naphthyl, which alkyl, phenyl or naphthyl is unsubstituted or substituted by F, Cl, Br, —OH, —CN, —NO$_2$, pheny or naphthyl, which phenyl or naphthyl is unsubstituted or substituted by F, Cl, Br, $C_1$–$C_{18}$-alkyl or —O—$C_1$–$C_{18}$-alkyl, a heterocyclic aromatic residue, —OCOR$_5$, —OR$_6$, —COOR$_5$, —N(R$_6$)(R$_7$) or —CON(R$_6$)(R$_7$), in which R$_5$ is $C_1$–$C_{18}$-alkyl, phenyl, naphthyl or benzyl, which alkyl, phenyl, naphthyl or benzyl is unsubstituted or substituted by F, Cl, Br, $C_1$–$C_{18}$-alkyl or —O—$C_1$–$C_{18}$-alkyl, and in which R$_6$ and R$_7$ are each independently of the other $C_1$–$C_{18}$-alkyl which is unsubstituted or substituted by —CN or —OH; $C_3$–$C_7$-cycloalkyl, phenyl or naphthyl, which cycloalkyl, phenyl or naphthyl is unsubstituted or substituted by F, Cl, Br, $C_1$–$C_{18}$-alkyl or —O—$C_1$–$C_{18}$-alkyl, or R$_6$ and R$_7$ together with the N atom form a 5-membered or 6-membered hetero ring; (vii) —OR$_8$, in which R$_8$ is $C_1$–$C_{18}$-alkyl, phenyl, naphthyl or $C_3$–$C_7$-cycloalkyl, which alkyl, phenyl, naphthyl or cycloalkyl is unsubstituted or substituted by F, Cl, Br, $C_1$–$C_{18}$-alkyl or —O—$C_1$–$C_{18}$-alkyl, or benzyl, (viii) —SR$_8$, (ix) —N(R$_6$)(R$_7$), (x) —COOR$_5$, (xi) —N(R$_9$)COR$_5$, in which R$_9$ is $C_1$–$C_{18}$-alkyl, phenyl, naphthyl or $C_3$–$C_7$-cycloalkyl, which alkyl, phenyl, naphthyl or cycloalkyl is unsubstituted or substituted by F, Cl, Br, $C_1$–$C_{18}$-alkyl or —O—$C_1$–$C_{18}$-alkyl, benzyl or the residue —COR$_5$, or in which R$_9$ together with the N atom form a heterocyclic ring, (xii) —N(R$_8$)COOR$_5$, (xiii) —NR$_8$CON(R$_6$)(R$_7$), (xiv) —SO$_2$R$_5$ or —SOR$_5$, (xv) —SO$_2$OR$_5$, (xvi) —CON(R$_6$)(R$_7$), (xvii) —SO$_2$N(R$_6$)(R$_7$), (xviii) —N=N-R$_{10}$, in which R$_{10}$ is the residue of a coupling component, or phenyl which is unsubstituted or substituted by F, Cl, Br, $C_1$–$C_{18}$-alkyl or —O—$C_1$–$C_{18}$-alkyl, or (xix) —OCOR$_5$, in which substituents (ix)-(xiv) R$_5$, R$_6$ and R$_7$ are as defined under (vi) and R$_8$ is as defined under (vii), except the compound in which R$_1$, R$_2$, R$_3$ and R$_4$ are H and Z is methyl.

2. A pigment according to claim 1, wherein in formula (I) Z is $C_1$–$C_{12}$-alkyl, and R$_1$, R$_2$, R$_3$ and R$_4$ are each independently of the other H, F, Cl, —CN, trifluoromethyl, $C_1$–$C_{12}$-alkyl, $C_1$–$C_{12}$-alkoxy, $C_1$–$C_{12}$-alkylmercapto, $C_2$–$C_{12}$-alkoxycarbonyl, $C_2$–$C_{24}$-dialkylamino, phenyl, phenoxy, phenylmercapto or phenoxycarbonyl, except the compound in which R$_1$, R$_2$, R$_3$ and R$_4$ are H and Z is methyl.

3. A pigment according to claim 1, wherein in formula (I) Z is $C_1$–$C_8$-alkyl, and R$_1$, R$_2$, R$_3$ and R$_4$ are each independently of the other H, F, Cl, —CN, trifluoromethyl, $C_1$–$C_8$-alkyl, $C_1$–$C_8$-alkoxy, $C_1$–$C_8$-alkylmercapto, $C_2$–$C_{16}$-dialkylamino or phenyl, except the compound in which R$_1$, R$_2$, R$_3$ and R$_4$ are H and Z is methyl.

4. A pigment according to claim 1, wherein in formula (I) Z is $C_1$–$C_4$-alkyl, R$_1$, R$_2$ and R$_4$ is H, and R$_3$ is H, Cl or $C_1$–$C_4$-alkyl, except the compound in which R$_1$, R$_2$, R$_3$ and R$_4$ are H and Z is methyl.

5. A process for producing the pigments according to claim 1 or the pigment represented by formula

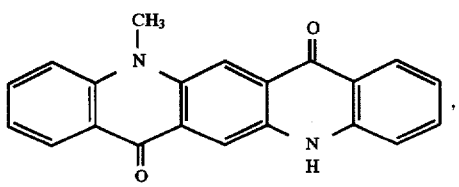

, characterized in that a quinacridone represented by formula II

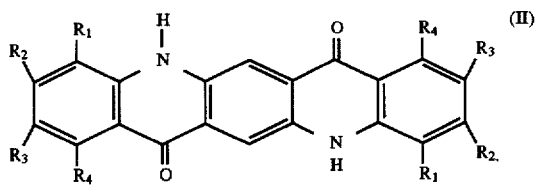

(II)

wherein $R_1$, $R_2$, $R_3$ and $R_4$ have the meaning given in claim 1, is subjected to a N-deprotonation reaction in an organic solvent using a base, and then subjected to an alkylation reaction using an alkylating agent.

6. A process according to claim 5, wherein said organic solvent is tetrahydrofuran, N,N-dimethylformamide, dioxane, dimethylsulfoxide, N,N-dimethylacetamide or N-methylpyrrolidone, or a mixture of at least two of them.

7. A process according to claim 5, wherein said base is at least one selected from the group consisting of alkali metals, alkali metal hydroxides and carbonates, and, anhydrous alkali metal hydrides.

8. A process according to claim 5, wherein said alkylating agent is at least one selected from the group consisting of halides of formula

ZX          (III), sulfonic acid esters of formula

A—SO$_2$—OZ     (IV), dialkyl carbonates of formula

Z—O—CO—O—Z    (V), dialkyl sulfates of formula

Z—O—SO$_2$—O—Z    (VI), oxonium salts of formula $(B_3O)^{\oplus}U^{\ominus}$   (VII), alkyl perchlorates of formula ZClO$_4$     (VIII)

and alkyl halogensulfonates of formula

X—SO$_2$—OZ     (IX), in which Z is $C_1$–$C_{18}$-alkyl which is unsubstituted or substituted by F, Cl, Br, —OH, —O—$C_1$–$C_{18}$-alkyl, $C_3$–$C_7$-cycloalkyl, phenyl or naphthyl, X is F, Cl, Br or I, A is H, $C_1$–$C_4$-alkyl or phenyl, which alkyl or phenyl is unsubstituted or substituted by F, Cl, Br or $C_1$–$C_4$-alkyl, B is H, Z, $C_5$–$C_7$-cycloalkyl or phenyl, which cycloalkyl or phenyl is unsubstituted or substituted by F, Cl, Br or $C_1$–$C_4$-alkyl, with the proviso that at least one of B is Z, and Y is $F^{\ominus}$, $Cl^{\ominus}$, $Br^{\ominus}$, $I^{\ominus}$, $BF_4^{\ominus}$, $PF_6^{\ominus}$, $AsF_6^{\ominus}$, $SbF_6^{\ominus}$, $FSO_3^{\ominus}$ or the anion of an organic sulfonic acid or carboxylic acid.

9. A process according to claim 8, wherein said alkylating agent is at least one selected from the group consisting of halides of formula (III) and dialkyl sulfates of formula (VI).

10. A process for separating the pigment according to claim 1 or the pigment represented by formula

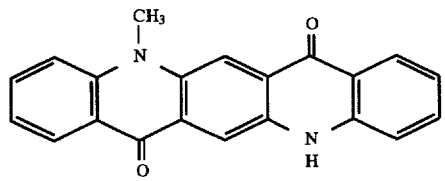

from a mixture composed of said pigment and its corresponding N,N'-dialkyl-quinacridone, characterized in that the mixture is reacted with a base in an organic solvent, the solid content left thereafter is removed by filtration, and then the filtrate is reacted with an acid.

11. A process according to claim 10, wherein said base is at least one selected from the group consisting of alkali metals, alkali metal hydroxides and carbonates, and anhydrous alkali metal hydrides.

12. A process according to claim 10, wherein said organic solvent is tetrahydrofuran, N,N-dimethylformamide, dioxane, dimethylsulfoxide, N,N-dimethylacetamide or N-methylpyrrolidone, or a mixture of at least two thereof.

13. A composition comprising a pigment according to claim 1 and an organic polymeric material.

14. A composition according to claim 13, wherein the high molecular weight organic material comprises a linear polyester.

15. A method of coloring a high molecular weight organic material, which comprises incorporating an effective amount of a pigment according to claim 1 or the pigment represented by the formula

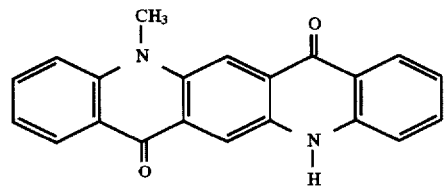

into said high molecular weight organic material.

16. A method of use of the pigment according to claim 1 or the pigment represented by the formula

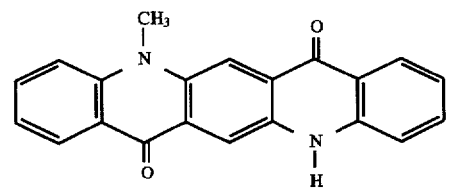

in an electroluminescent element comprising an anode, a hole transporting layer, a light emitting layer and a metal cathode, which comprises incorporating an effective amount of a pigment according to claim 1 or the pigment represented by the formula

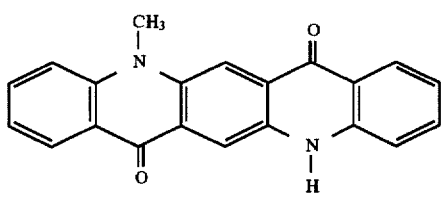

into said electroluminescent element as the light emitting layer.

17. A method of use of the pigment according to claim 1 or the pigment represented by the formula

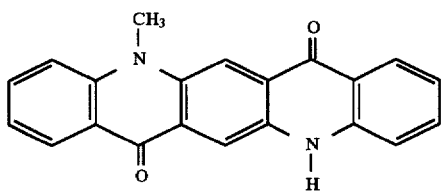

in an electrophotographic photoreceptor comprising a metallic substrate and thereon a photoconductive layer and a charge transporting layer, which comprises incorporating an effective amount of a pigment according to claim 1 or the pigment represented by formula

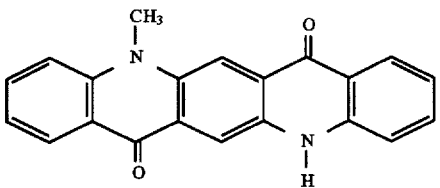

into said electrophotographic photoreceptor as the photoconductive layer.

* * * * *